United States Patent [19]

Dedo

[11] 4,052,753
[45] Oct. 11, 1977

[54] KNEE SPACER AND METHOD OF REFORMING SLIDING BODY SURFACES

[76] Inventor: Richard G. Dedo, 8629 La Losa Drive, West, Jacksonville, Fla. 32217

[21] Appl. No.: 710,402

[22] Filed: Aug. 2, 1976

[51] Int. Cl.² .................. A61F 1/00; A61F 1/24
[52] U.S. Cl. ........................................ 3/1; 3/1.91;
3/1.911; 128/92 C
[58] Field of Search ................... 3/1, 1.9–1.913;
128/92 C

[56] References Cited

U.S. PATENT DOCUMENTS

| 3,577,837 | 5/1971 | Bader | 3/1.9 |
| 3,842,441 | 10/1974 | Kaiser | 3/1 |

FOREIGN PATENT DOCUMENTS

| 2,232,002 | 1/1973 | Germany | 128/92 C |

Primary Examiner—Ronald L. Frinks
Attorney, Agent, or Firm—Powell L. Sprunger

[57] ABSTRACT

A knee spacer comprising, an elongated member of a flexible and relatively biologically inert material for placement in the space normally occupied by the suprapatellar pouch of a patient's knee.

21 Claims, 8 Drawing Figures

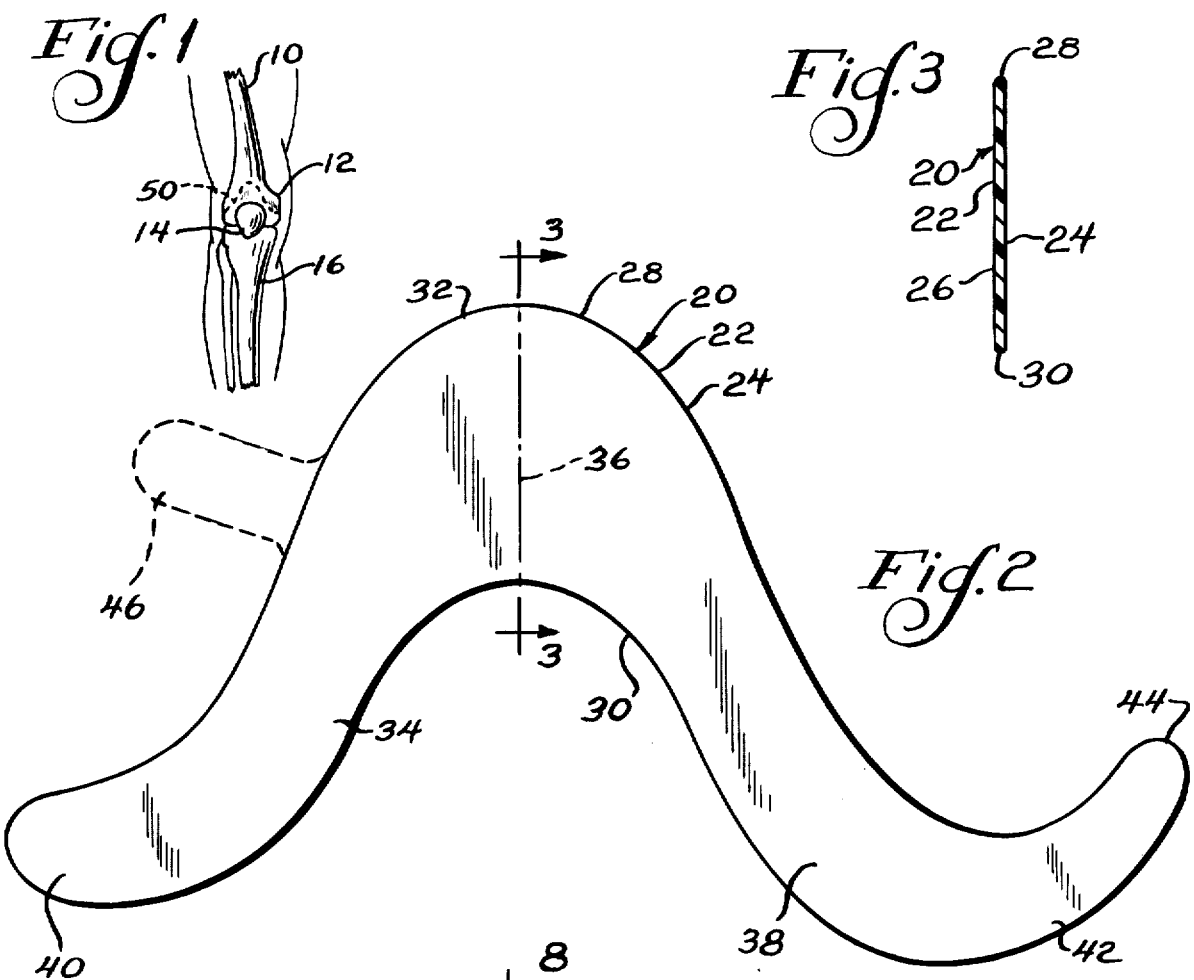
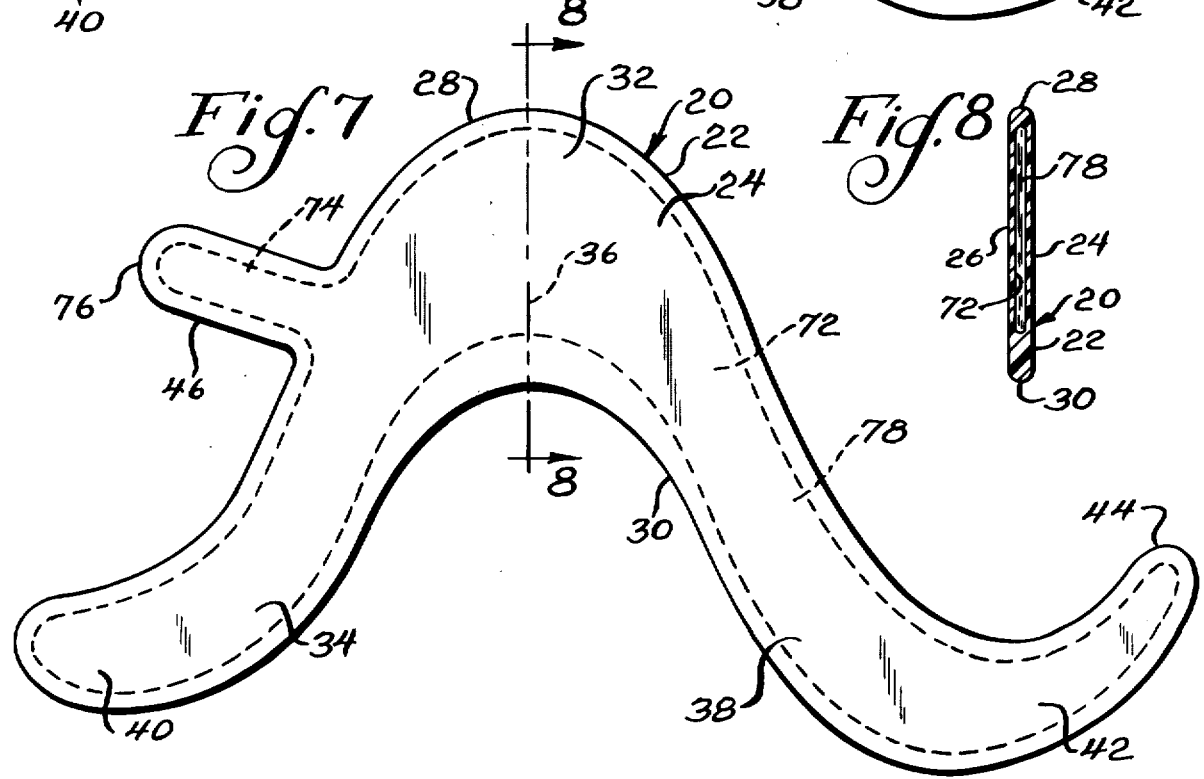

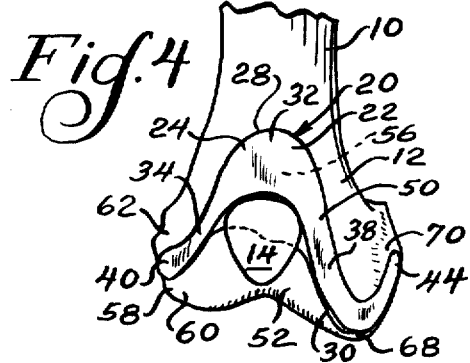
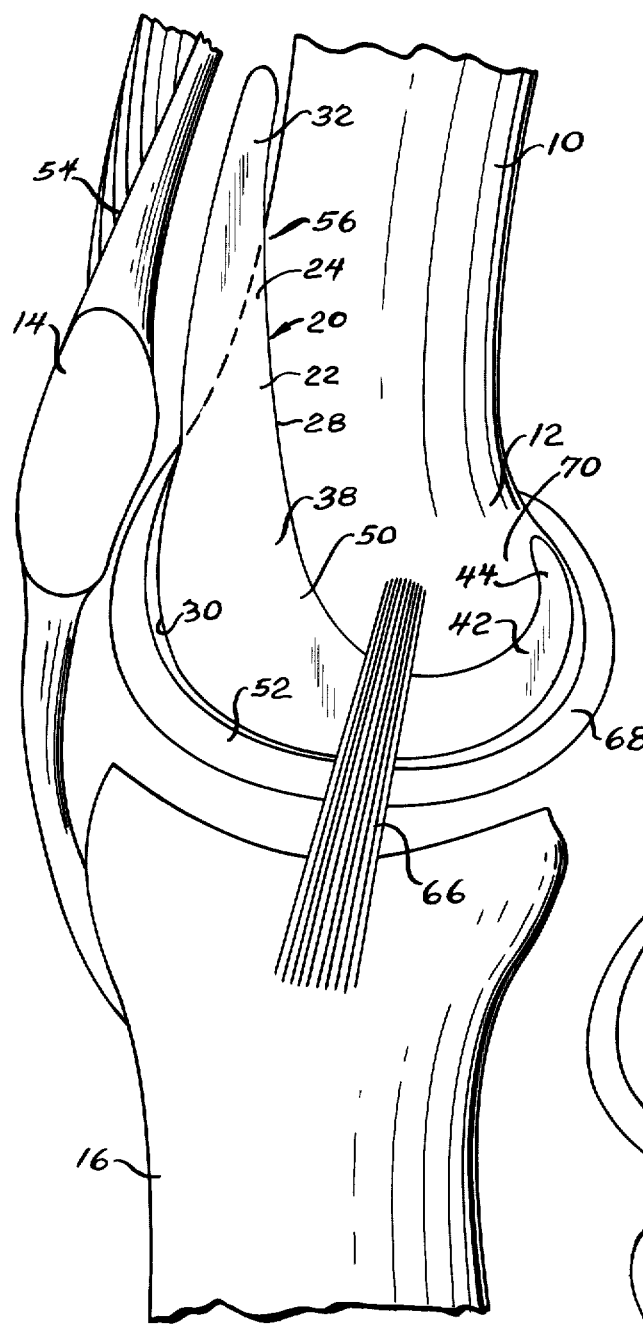
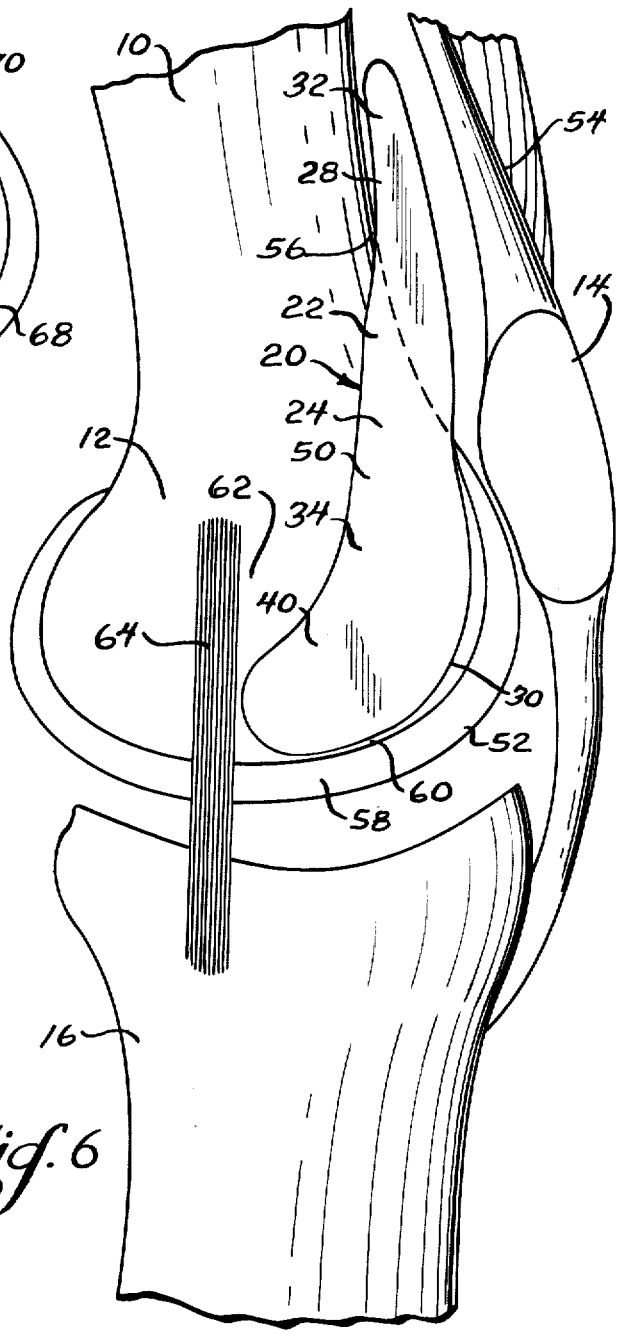

KNEE SPACER AND METHOD OF REFORMING SLIDING BODY SURFACES

BACKGROUND OF THE INVENTION

The present invention relates to therapeutic devices for a patient's body, and more particularly to such devices for the knee.

During normal operation of the knee, a potential space above and adjacent the patella, termed the suprapatellar pouch, provides a sliding mechanism for tendons to permit flexation and extension of the knee. During knee surgery, e.g., a total replacement procedure when the lower part of the femur and the upper part of the tibia are replaced, or synovectomy when the synovium is removed, the suprapatellar pouch may be partially or totally destroyed. As a result, during healing of the knee after surgery, opposed surfaces between tendons and the distal femur become adhered together in the region normally occupied by the pouch, thus preventing movement of the tendons relative the distal femur and normal operation of the knee. Accordingly, after a period of healing, forced flexation of the knee is required under anesthesia during which the adhered surfaces are virtually ripped apart in order to permit voluntary movement of the knee by the patient. Such a procedure not only poses inconvenience and an undesired trauma to the patient, such adhesions impair satisfactory rehabilitation and motion of the patient's knee.

SUMMARY OF THE INVENTION

A principal feature of the present invention is the provision of a spacer to enhance healing and rehabilitation of a patient's knee after surgery.

The knee spacer of the present invention comprises, an elongated member of a flexible and relatively biologically inert material having a front surface, a back surface, and side edges defining a shape similar to the contour of the suprapatellar pouch of the patient's knee superior the articular cartilage. The member is placed during surgery in the space normally occupied by the pouch.

A feature of the present invention is that the member prevents adhesion of opposed body surfaces between tendons and the femur after surgery.

Another feature of the invention is that body tissues do not grow into or on the surfaces of the member, and the member causes the body to form sliding surfaces adjacent the member surfaces during the healing process.

Yet another feature of the invention is that the member may be readily removed from the patient's knee after formation of sliding surfaces by the patient's body.

Still another feature of the invention is that the member eliminates the necessity for the surgeon to rupture adhesions intermediate tendons and the distal femur after surgery.

A further feature of the invention is that the member facilitates normal operation of the knee after removal.

In an embodiment of the invention the member may have a filled chamber which serves to maintain a desired shape of the member during use.

Still another feature of the invention is that a medium in the chamber may be removed from the member in order to facilitate removal of the member from the patient's knee.

Another feature of the invention is the provision of methods for preventing adhesions and reforming sliding surfaces in a body.

Further features will become more fully apparent in the following description of the embodiments of this invention and from the appended claims.

DESCRIPTION OF THE DRAWINGS

In the drawings:

FIG. 1 is a fragmentary front or anterior diagrammatic view of a patient's knee;

FIG. 2 is a plan view of a knee spacer of the present invention;

FIG. 3 is a sectional view taken substantially as indicated along the line 3—3 of FIG. 2;

FIG. 4 is a fragmentary front or anterior view showing the knee spacer as positioned in a configuration overlying the distal femur;

FIG. 5 is a fragmentary medial side view showing the knee spacer as positioned in the patient's knee;

FIG. 6 is a fragmentary lateral side view showing the knee spacer as positioned in the patient's knee;

FIG. 7 is a plan view of another embodiment of the spacer of the present invention; and FIG. 8 is a sectional view taken substantially as indicated along the line 8—8 of FIG. 7.

DESCRIPTION OF THE PREFERRED EMBODIMENTS

Referring now to FIG. 1, there is shown the right knee of a patient including the femur 10, the distal femur 12, the patella or knee cap 14, and the tibia 16. Although for convenience the invention will be described primarily in connection with the patient's right knee, it will be understood that the device of the invention is equally applicable to the patient's left knee by suitable modification or inversion of the device.

Referring now to FIGS. 2 and 3, there is shown a knee spacer generally designated 20 which is made of a flexible and relatively biologically inert material, such as silicone. The spacer 20 comprises a generally planar elongated member or insert 22 having a generally smooth front surface 24, a generally smooth back surface 26, an upper or superior edge 28, and a lower or inferior edge 30. the member 22 has an arcuate central portion 32, a first leg or wing 34 extending laterally and inferiorly from the central portion 32 at a generally acute angle relative a longitudinal central reference line 36 of the central portion 32, and a second opposed leg or wing 38 extending inferiorly and medially from the central portion 32 at a generally acute angle relative the reference line 36. As shown, the first leg 34 is slightly curved superiorly or upwardly adjacent an outer end 40 of the first leg 34, and the second leg 38 has an upturned or superiorly directed end portion 42 adjacent an outer end 44 of the second leg 38, such that the second leg 38 is curved adjacent its outer end 44. Also, the length of the second leg 38 is greater than the length of the first leg 34, the lowermost portion or edge of the first leg 34 is located above the lowermost portion or edge of the second leg 38, and the width of the member 22 is substantially greater than the thickness of the member throughout a substantial extent of the central portion 32 and first and second legs 34 and 38. Also, as shown, the first and second legs 34 and 38 have a taper in width from the central portion 32 to their respective outer ends 40 and 44.

The member 22 may also have a tab 46 directed outwardly from one of the legs 34 and 38 for a purpose which will be described below. In the embodiment shown, the tab 46 extends laterally from a side of the first leg 34.

With reference to FIGS. 1, and 4–6, an upper portion of the suprapatellar pouch 50, i.e., a potential space, in the knee is located above and adjacent the patella 14 and superior the femoral articular cartilage 52. During normal operation of the knee, the suprapatellar pouch 50 provides sliding surfaces for tendons, such as the quadriceps 54, to permit flexation and extension of the knee. However, during knee surgery, such as a total replacement procedure when the lower part of the femur 10 and the upper part of the tibia 16 are replaced, or synovectomy when the synovium is removed, the suprapatellar pouch may be partially or totally destroyed, and may fill with body fluids, such as blood. As a result, during healing of the knee after surgery, opposed surfaces between the tendons and distal femur become adhered together in the region normally occupied by the suprapatellar pouch 50, thus preventing normal operation of the knee. Accordingly, after a period of healing, forced flexation of the knee is required under anesthesia during which the adhered surfaces are ripped apart in order to permit voluntary movement of the knee by the patient.

In accordance with the present invention, with reference to FIGS. 4–6, the member 22 has a shape similar to the normal contour of the suprapatellar pouch 50 superior the articular cartilage 52, and the member 22 is placed in this portion of the pouch 50 during surgery, such that the member is located in the space normally occupied by the suprapatellar pouch superior the femoral articular cartilage and in a configuration overlying the distal femur 12. Thus, with reference to FIG. 4, the central portion 32 of the member 22 covers or overlies an anterior central portion 56 of the distal femur 12. With reference to FIGS. 4 and 6, the first leg 34 extends inferiorly and laterally on the right knee from the central portion 32 to a location intermediate the lateral femoral articular cartilage 58 of th lateral condyle 60 and the lateral epicondyle 62, with the outer end 40 of the first leg 34 extending to the insertion of the tendon of the popliteus muscle and short of the lateral collateral ligament 64. With reference to FIGS. 4 and 5, the second leg 38 extends inferiorly and medially from the central portion 32 beneath the medial collateral ligament 66 to a location intermediate the medial femoral articular cartilage 68 and the medial epicondyle 70.

After surgery, the knee spacer 20 remains in the space normally occupied by the suprapatellar pouch 50 for a period of time, such as two to three weeks, and, since the spacer material is biologically inert, body tissues do not grow into or on the surfaces of the spacer. Rather, the body causes growth of linings adjacent the opposed surfaces of the knee spacer, and reforms the sliding surfaces of the knee above and adjacent the patella. After a sufficient length of time has passed to form the sliding surfaces, the surgeon may make an incision under local anesthetic to remove the flexible member 22 from the knee. In a preferred form the spacer has the tab 46, as previously discussed in connection with FIGS. 2 and 3, and the surgeon may palpate the skin in order to determine the location of the tab, after which the incision is made in the locality of the tab and the spacer is removed through use of the tab 46. After removal of the spacer from the knee, the necessary sliding surfaces between the tendons and distal femur have been formed as a result of placement of the spacer in the knee, thus facilitating healing and rehabilitation of the knee after surgery. Moreover, the device of the present invention eliminates the necessity for the surgeon to break adhesions between the surfaces intermediate the tendons and femur by forced flexation of the knee.

In accordance with methods of the present invention for preventing adhesions of the knee after surgery, an insert of a flexible and relatively biologically inert material is placed in a region of the body normally occupied by the suprapatellar pouch, and the insert is removed after formation of sliding surfaces by the body adjacent the insert. In accordance with another method of the present invention, an elongated insert of a flexible and relatively biologically inert material is placed in the suprapatellar pouch at a location superior the femoral articular cartilage and overlying a region of the distal femur including an anterior central portion of the distal femur and extending laterally and inferiorly from the central portion to a location intermediate the lateral femoral articular cartilage of the lateral condyle and the lateral epicondyle, and medially and inferiorly from the central portion to a location intermediate the medial femoral articular cartilage and the medial epicondyle. The insert is removed after formation of sliding surfaces by the body adjacent the insert. In accordance with a method of reforming normally sliding surfaces of a body, an insert of a flexible and relatively biologically inert material is placed between the body surfaces for a period of time until the sliding surfaces have been substantially reformed, and the insert is removed from the body.

Another embodiment of the present invention is illustrated in FIGS. 7 and 8, in which like reference numerals designate like parts. In this embodiment, the member 22 has a chamber 72 which extends throughout a substantial extent of the central portion 32, and the first and second legs 34 and 38, respectively. As shown, sides of the chamber 72 are slightly spaced from the superior and inferior edges 28 and 30. The tab 46 has a channel 74 communicating with the chamber 72, and, in a preferred form, the outer end 76 of the tab 46 is closed. Thus, in a preferred form, the chamber 72 is prefilled with a medium 78, such as a saline solution of silicone gel, e.g., a semi-fluid silicone of liquid methyl silicone resin, in the case of use of a silicone material for walls of the member 22.

In use, the hollow member 22 of FIGS. 7 and 8 causes passage of the medium 78 from the central portion 32 into the first and second legs 34 and 38 during flexation of the knee in order to maintain the legs in their desired positions, and the medium 78 passes superiorly from the legs 34 and 38 into the central portion 32 when the knee is passively extended. Accordingly, the filled chamber facilitates maintenance of the knee spacer in its desired shape. Additionally, during removal of the hollow member 22 from the knee, the outer end 76 of the tab 46 may be severed in order to remove the medium 78 from the chamber 72, and facilitate removal of the member 22 from the knee due to collapse of the flexible member 22 when the medium 78 is removed from the chamber 72.

The foregoing detailed description is given for clearness of understanding only, and no unnecessary limitations should be understood therefrom, as modifications will be obvious to those skilled in the art.

I claim:

1. A knee spacer comprising, an elongated member of a flexible and relatively biologically inert material having a front surface, a back surface, and side edges defining a shape similar to the normal contour of the suprapatellar pouch of a human knee superior the femoral articular cartilage.

2. A knee spacer for placement in the suprapatellar pouch of a patient's knee comprising, an elongated member of a flexible and relatively biologically inert material having a back surface facing the distal femur after placement of the member, a front surface facing away from the distal femur after placement of the member, a central portion for placement over an anterior central portion of the distal femur at a location superior the femoral articular cartilage, a first side leg extending laterally and inferiorly from said central portion for placement intermediate the lateral femoral articular cartilage of the lateral condyle and the lateral epicondyle, and a second side leg extending medially and inferiorly from said central portion for placement intermediate the medial femoral articular cartilage and the medial epicondyle.

3. A knee spacer for placement in the suprapatellar pouch of a patient's knee comprising, an elongated member of a flexible and relatively biologically inert material having a front surface, a back surface, and superior and inferior edges defining a central portion for placement over an anterior central portion of the distal femur, a first leg extending laterally and inferiorly from said central portion relative the femur, and a second leg extending medially and inferiorly from said central portion relative the femur.

4. The spacer of claim 3 wherein said material is silicone.

5. The spacer of claim 3 wherein said first leg has a slight taper in width from said central portion toward an outer end of said first leg.

6. The spacer of claim 3 wherein said first leg has a slight superior curve adjacent an outer end of the first leg.

7. The spacer of claim 3 wherein said second leg has a taper in width from said central portion toward an outer end of said second leg.

8. The spacer of claim 3 wherein said second leg has a superior curve adjacent an outer end of the second leg.

9. The spacer of claim 3 wherein said second leg has a superiorly directed outer end.

10. The spacer of claim 3 wherein an inferior-most edge of the first leg is superior an inferior-most edge of the second leg.

11. The spacer of claim 3 wherein at least one of said legs has an outwardly directed tab.

12. The spacer of claim 11 wherein said tab is laterally directed from said first leg.

13. The spacer of claim 3 wherein said spacer has a chamber.

14. The spacer of claim 13 wherein said chamber extends from said central portion toward outer ends of said first and second legs.

15. The spacer of claim 14 wherein said chamber is spaced slightly from said superior and inferior edges.

16. The spacer of claim 13 wherein said chamber is prefilled with a medium.

17. The spacer of claim 13 including a hollow tab extending outwardly from one of said legs and defining a channel communicating with said chamber.

18. A knee spacer for placement in the suprapatellar pouch of a patient's knee comprising, an elongated generally planar member of a flexible and relatively biologically inert material having a generally smooth front surface, a generally smooth back surface, an upper and lower edge defining an arcuate central portion, a first leg extending from said central portion generally at an acute angle relative a longitudinal central reference line of said central portion, and an opposed second leg extending from said central portion generally at an acute angle relative the central reference line of said central portion, said first leg having a slight upper curve adjacent an outer end of the first leg, said second leg having an upturned outer end, said second leg having a greater length than the first leg, said member having a substantially greater width than thickness throughout a substantial extent of said central portion and first and second legs, and the lowermost portion of the first leg being located above the lowermost portion of the second leg.

19. A method of preventing adhesions in a knee after surgery, comprising the steps of:
    placing an insert of a flexible and relatively biologically inert material having a pair of opposed smooth surfaces in a region of the body normally occupied by the suprapatellar pouch so that said smooth surfaces are interposed between body surfaces; and
    removing the insert after formation of sliding surfaces by the body adjacent the insert.

20. A method of preventing adhesions in a knee after surgery, comprising the steps of:
    placing an elongated insert of a flexible and relatively biologically inert material in the suprapatellar pouch at a location superior the femoral articular cartilage and overlying a region of the distal femur including an anterior central portion of the distal femur and extending laterally and inferiorly from the central portion to a location intermediate the lateral femoral articular cartilage of the lateral condyle and the lateral epicondyle, and medially and inferiorly from the central portion to a location intermediate the medial femoral articular cartilage and the medial epicondyle; and
    removing the insert after formation of sliding surfaces by the body adjacent the insert.

21. A method of reforming normally sliding surfaces of a body, comprising the steps of:
    placing an insert of a relatively biologically inert material having a pair of opposed smooth surfaces between the body surfaces for a period of time while separating the body surfaces by the insert throughout a substantial area of the body surfaces until the sliding surfaces have been substantially reformed; and
    removing the insert from the body.

* * * * *